United States Patent [19]

Krishnamurti et al.

[11] Patent Number: 5,336,808
[45] Date of Patent: Aug. 9, 1994

[54] PROCESS FOR THE PREPARATION OF 3,5-DIAMINOBENZOTRIFLUORIDE

[75] Inventors: Ramesh Krishnamurti, Amherst, N.Y.; Mahendra K. Dosi, Alpharetta, Ga.; Henry C. Lin, Grand Island, N.Y.

[73] Assignee: Occidental Chemical Corporation, Niagara Falls, N.Y.

[21] Appl. No.: 624,846

[22] Filed: Dec. 10, 1990

[51] Int. Cl.$^5$ ............................................. C07C 209/36
[52] U.S. Cl. .................................... 564/412; 564/416
[58] Field of Search .............................. 564/412, 416

[56] References Cited

U.S. PATENT DOCUMENTS 4,792,625  12/1988  Wiener et al. ........................ 564/416

FOREIGN PATENT DOCUMENTS 1458633  12/1976  United Kingdom ........... C07C 1/26

OTHER PUBLICATIONS

Chang. "Physical Chemistry with Applications to Biological Systems" 2nd Ed. pp. 328–330 (1981).

Primary Examiner—Glennon H. Hollrah
Assistant Examiner—Brian M. Burn
Attorney, Agent, or Firm—Arthur S. Cookfair; Wayne A. Jones

[57] ABSTRACT

3,5-Diaminobenzotrifluoride is prepared by reaction of 4-chloro-3,5-dinitrobenzotrifluoride with sodium formate in acetic acid, in the presence of sodium acetate and palladium on charcoal.

10 Claims, No Drawings

PROCESS FOR THE PREPARATION OF 3,5-DIAMINOBENZOTRIFLUORIDE

BACKGROUND OF THE INVENTION

1. Field of the Invention

This invention relates to a process for the preparation of 3,5-diamino benzotrifluoride by reduction of 4-chloro-3,5-dinitrobenzotrifluoride. The diamino product of this invention is a valuable chemical intermediate, useful in a variety of organic syntheses. In particular, the diamino product may be employed as a monomer in the preparation of various polymers including polyurethanes and polyimides.

2. Description of the Prior Art

The reduction of aromatic nitro compounds is an important and widely used commercial method for the preparation of aromatic amines. It is known that the nitro group may readily be reduced by various reagents, including iron or tin and hydrochloric acid or sodium sulfide. Catalytic hydrogenation using various hydrogenation catalysts is also known. However, the reduction of aromatic nitro compounds containing ring halogen substituent(s) is unpredictable.

Bouchet, et al., Syn. Commun., 4, 57–9 (1974), disclose the reduction of para-chloronitrobenzene to para-chloroaniline, using hydrogen in the presence of a palladium on carbon catalyst.

According to A. Weizmann (J. Am. Chem. Soc., 71, 4154, 1949)), the catalytic hydrogenation of diethylaminoethyl 4-nitro-2-chlorobenzoate using palladium on barium sulfate as a catalyst was impractical from a preparative point of view. The nitro compound was often incompletely reduced. The chlorine was occasionally removed from the ring while in other reactions it remained on the ring. Similar hydrogenation experiments conducted with 4-nitro-2-chlorobenzoic acid and its ethyl ester, using palladium on barium sulfate as a catalyst, produced variable results depending upon the solvent employed.

British Pat. No. 1457608 discloses processes for reducing nitroaromatic water-insoluble compounds by contacting the compounds with an aqueous solution of a formic acid salt in the presence of a heterogeneous hydrogenation catalyst and a surface active agent, particularly a phase transfer catalyst.

British Pat. No. 1458633 discloses a process for dehalogenating water-immiscible aromatic compounds by contacting the said compound with an aqueous solution of a formic acid salt in the presence of a hydrogenation catalyst and a surface active agent or a phase transfer catalyst.

U.S. Pat. No. 4,792,625 discloses a process for reducing substantially water-insoluble nitroaromatic compounds to the corresponding amine by contacting an aqueous solution of a formic acid salt, e.g., potassium formate, with an organic solution of the nitroaromatic compound in the presence of a hydrogenation catalyst, e.g., palladium on carbon. The process is carried out in a water-insoluble organic solvent such as toluene, benzene, xylene, or preferably an alcohol, e.g., ethanol, propanol, etc.

SUMMARY OF THE INVENTION

It has now been found that 3,5-diaminobenzotrifluoride (3,5-DABTF) may be conveniently prepared from 4-chloro-3,5-dinitrobenzotrifluoride in a one-step dehalogenation/reduction process which comprises contacting a solution of 4-chloro-3,5-dinitrobenzotrifluoride in anhydrous acetic acid with an alkali metal formate in the presence of an alkali metal acetate and palladium on carbon catalyst. The process may be carried out by adding the alkali metal formate, either in anhydrous form, or preferably, as an aqueous solution, to the acetic acid solution, with stirring.

DETAILED DESCRIPTION OF THE INVENTION

The alkali metal acetate is preferably employed in an amount of at least one molar equivalent. Greater amounts may be employed but are not necessary. When insufficient amounts are employed, the excess HCl formed during the reaction will interfere with the catalytic process. The preferred alkali metal acetate is sodium acetate.

The alkali metal formate, preferably sodium formate, may be added in dry form, such as in powder form, or preferably, as an aqueous solution. In a preferred embodiment, water is added to the acetic acid solution in an amount sufficient to provide a volume ratio of acetic acid/water of between about 30/70 and 70/30. The preferred ratios are from about 60/40 to about 40/60.

The process is normally carried out at a temperature ranging from about 0° C. to about 50° C. and most preferably about 35° to 45° C. Higher temperatures tend to lead to the production of undesired products such as phenols.

The following examples are provided to further illustrate this invention and the manner in which it may be carried out. It will be understood, however, that the specific details given in the examples have been chosen for purposes of illustration only and are not to be construed as limiting the invention. In the examples, unless otherwise indicated, all parts and percentages are by weight and all temperatures are in degrees Celsius.

EXAMPLE 1

Preparation of 3,5DABTF Under Anhydrous Conditions

Sodium formate (12.24 g) was added to a mixture of 4-chloro-3,5-dinitrobenzotrifluoride (5.41 g), sodium acetate (1.64 g) and 5% Pd/C (0.5 g) in glacial acetic acid (60 mL). The mixture was stirred and the resultant exotherm, which lasted about an hour, was controlled by cooling to maintain a reaction temperature of about 40° C. As the exotherm subsided, external heating was applied to maintain the temperature at about 40° C. Gas chromatographic analysis of the reaction mixture, at the end of one hour, indicated diaminobenzotrifluoride as the major component (35%) with no 4-chloro-3,5-dinitrobenzotrifluoride remaining. The maximum amount (about 45%) of 3,5-diaminobenzotrifluoride formed after 2 hours after which it was converted to other undesirable products.

EXAMPLE 2

Preparation of 3,5-DABTF Using 60/40 Acetic Acid/water

Sodium formate (81.6 g) was added, with stirring, to a mixture of 4-chloro-3,5-dinitrobenzotrifluoride (54.1 g), sodium acetate (16.4 g) and 5% Pd/C in glacial acetic acid (400 mL). Evolution of gas was observed. The reaction mixture was stirred and cooled to maintain a reaction temperature of about 40° C. over a period of about 2.5 hours, during which time the mixture became progressively viscous. Additional sodium formate (40.8 g), as solution in 250 mL of water, was added over a 15 minute period. Gas evolution increased. The temperature was maintained at about 40° C, with cooling, for an additional half hour then with external heating for about 3 hours. Analysis of the reaction mixture by gas chromatography indicated the major product (85%) to be 3,5-diaminobenzotrifluoride, with no starting material remaining.

EXAMPLE 3

Preparation of 3,5-DABTF Using 60/40 Acetic Acid/water

Following the general procedure of Example 2: 4-chloro-3,5-dinitrobenzotrifluoride (5.41 g), sodium acetate (1.64 g) glacial acetic acid (40 mL) and 5% Pd/C (0.5 g) were combined and treated with powdered sodium formate (8.16 g). After 2.5 hours an aqueous solution of sodium formate (2.7 g in 30 mL of water) was added and the mixture maintained at 40° C. for 3 hours. GC analysis of the crude reaction product indicated 90% (GC area %) 3,5-DABTF.

EXAMPLE 4

Preparation of 3,5-DABTF Using 50/50 Acetic Acid/water

To a mixture of 4-chloro-3,5-dinitrobenzotrifluoride (5 g), sodium acetate (1.52 g), glacial acetic acid (37 mL) and 5% Pd/C (0.5 g) was added, with stirring, over a 45 minute period, a solution of sodium formate (11.29 g) in water (37 mL). A steady gas evolution was observed. The mixture was maintained, with stirring, at a temperature of about 40° C. for two hours. GC analysis of the reaction mixture indicated (in GC area %) 96% 3,5-DABTF. The remainder was primarily 4-chloro-3,5-DABTF.

What is claimed is:

1. A process for the preparation of 3,5-diamino benzotrifluoride comprising reacting 4-chloro-3,5-dinitro benzotrifluoride, as a solution in acetic acid, with an alkali metal formate in the presence of an alkali metal acetate and palladium on carbon catalyst.

2. A process according to claim 1 wherein the alkali metal formate is sodium formate.

3. A process according to claim 2 wherein the alkali metal acetate is sodium acetate.

4. A process according to claim 3 carried out at a temperature of about 0° to 50° C.

5. A process according to claim 4 carried out under anhydrous conditions.

6. A process according to claim 4 wherein an aqueous solution of sodium formate is added to a solution of 4-chloro-3,5-dinitrobenzotrifluoride in glacial acetic acid.

7. A process according to claim 4 wherein acetic acid and water are present in the ratio of from about 70/30 to 30/70 acetic acid/water.

8. A process according to claim 7 carried out at a temperature of about 35° to 45° C.

9. A process according to claim 8 wherein acetic acid and water are present in the ratio of from about 60/40 to 40/60 acetic acid/water.

10. A process for the preparation of 3,5-diamino benzotrifluoride comprising adding an aqueous solution of sodium formate to a solution of 4-chloro-3,5-dinitro benzotrifluoride in glacial acetic acid and reacting in the presence of sodium acetate and palladium on carbon catalyst.

* * * * *